US00PP36093P2

(12) United States Plant Patent
Koot

(10) Patent No.: US PP36,093 P2
(45) Date of Patent: Sep. 3, 2024

(54) ***PETUNIA* PLANT NAMED 'Dopetswepursta'**

(50) Latin Name: ***Petunia* X *hybrida***
Varietal Denomination: Dopetswepursta

(71) Applicant: DUMMEN GROUP B.V., De Lier (NL)

(72) Inventor: Arjan Koot, Oeffelt (NL)

(73) Assignee: DUMMEN GROUP S.V., De Lier (NL)

( * ) Notice: Subject to any disclaimer, the term of this patent is extended or adjusted under 35 U.S.C. 154(b) by 0 days.

(21) Appl. No.: 18/384,871

(22) Filed: Oct. 29, 2023

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.1, 356.13
See application file for complete search history.

*Primary Examiner* — Susan McCormick Ewoldt
(74) *Attorney, Agent, or Firm* — C. Anne Whealy

(57) ABSTRACT

A new and distinct cultivar of *Petunia* plant named 'Dopetswepursta', characterized by its compact and uniformly mounding plant habit; moderately vigorous growth habit and moderate growth rate; freely branching habit; early and freely flowering habit; large reddish purple-colored flowers with a white-colored star-shaped pattern; and good container and garden performance.

2 Drawing Sheets

Figure 1:
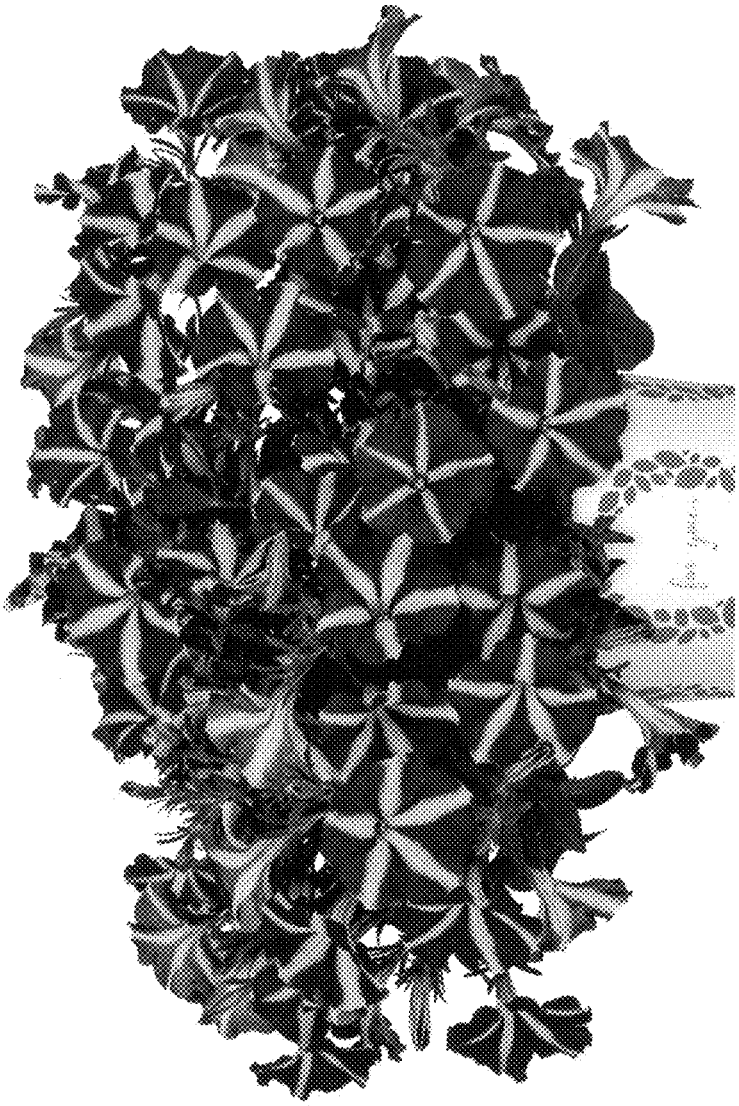

Botanical designation: *Petunia* X *hybrida.*
Cultivar denomination: 'DOPETSWEPURSTA'.

BACKGROUND OF THE INVENTION

The present invention relates to a new and distinct cultivar of *Petunia* plant, botanically known as *Petunia* X *hybrida* and hereinafter referred to by the name 'Dopetswepursta'.

The new *Petunia* plant is a product of a planned breeding program conducted by the Inventor in Rheinberg, Germany. The objective of the breeding program is to create new compact, freely branching and early-flowering *Petunia* plants with numerous attractive flowers.

The new *Petunia* plant originated from a cross-pollination made by the Inventor in July, 2020 in Rheinberg, Germany of a proprietary selection of *Petunia* X *hybrida* identified as code number TT20-K0749, not patented, as the female, or seed, parent with a proprietary selection of *Petunia* X *hybrida* identified as code number TT20-K0509, not patented, as the male, or pollen, parent. The new *Petunia* plant was discovered and selected by the Inventor as a single flowering plant from within the progeny of the stated cross-pollination in a controlled greenhouse environment in Rheinberg, Germany in May, 2021.

Asexual reproduction of the new *Petunia* plant by terminal vegetative cuttings in a controlled greenhouse environment in Rheinberg, Germany since May, 2021 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetswepursta'. These characteristics in combination distinguish 'Dopetswepursta' as a new and distinct *Petunia* plant:

1. Compact and uniformly mounding plant habit.
2. Moderately vigorous growth habit and moderate growth rate.
3. Freely branching habit.
4. Early and freely flowering habit.
5. Large reddish purple-colored flowers with a white-colored star-shaped pattern.
6. Good container and garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are denser than and not as open as plants of the female parent selection.
2. Flowers of plants of the new *Petunia* are more rounded and not as ruffled as flowers of plants of the female parent selection.
3. Flowers of plants of the new *Petunia* resist fading better than flowers of plants of the female parent selection.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are denser than and not as open as plants of the male parent selection.
2. Plants of the new *Petunia* are more freely flowering than plants of the male parent selection.
3. Flowers of the new *Petunia* are reddish purple in color with a white-colored star-shaped pattern whereas flowers of plants of the male parent selection are pink in color with a white-colored star-shaped pattern.
4. Plants of the new *Petunia* have longer peduncles than plants of the male parent selection.

Plants of the new *Petunia* can be compared to plants of *Petunia sensu* 'Dancasbipas', disclosed in U.S. Plant Pat. No. 16,386. In side-by-side comparisons, plants of the new *Petunia* and 'Dancasbipas' differ primarily in the following characteristics:

1. Plants of the new *Petunia* are more freely flowering than plants of 'Dancasbipas'.
2. Plants of the new *Petunia* have larger flowers than plants of 'Dancasbipas'.
3. Flowers of the new *Petunia* are reddish purple in color with a white-colored star-shaped pattern whereas flowers of plants of 'Dancasbipas' are pink in color with a white-colored star-shaped pattern.
4. Plants of the new *Petunia* are resistant to Tobacco Mosaic Virus whereas plants of 'Dancasbipas' are not resistant to Tobacco Mosaic Virus.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'Dopetswepursta' grown in a container.

Figure 2:
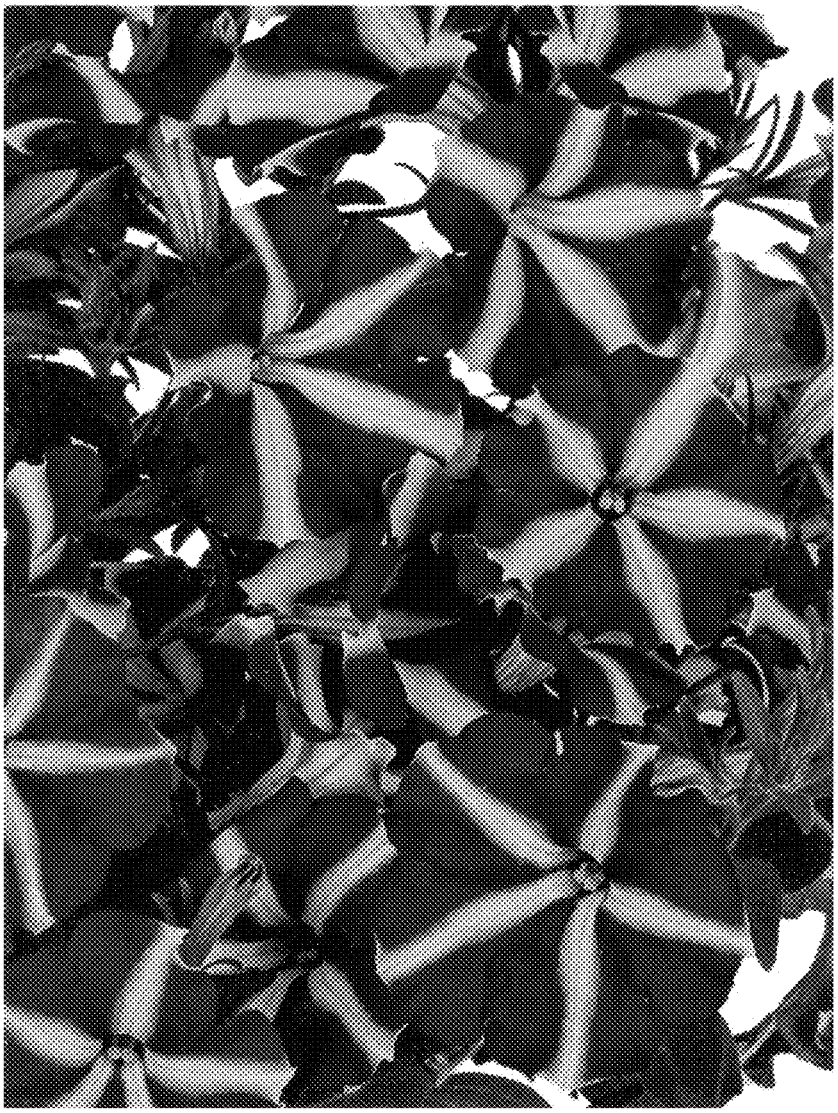

The photograph on the second sheet (FIG. 2) is a close-up view of typical flowers of 'Dopetswepursta'.

DETAILED BOTANICAL DESCRIPTION

The aforementioned photographs and following observations, measurements and values describe plants grown during the spring and summer in 22-cm containers in a glass-covered greenhouse in Rheinberg, Germany and under cultural practices typical of commercial *Petunia* production. During the production of the plants, day and night temperatures averaged 18C and light levels averaged 4,500 lux. Plants were twelve weeks old when the photographs were taken and 25 weeks old when the description was taken. In the following description, color references are made to The Royal Horticultural Society Colour Chart, Fifth Edition, except where general terms of ordinary dictionary significance are used.

Botanical classification: *Petunia* X *hybrida* 'Dopetswepursta'.

Parentage:

*Female, or seed, parent.*—Proprietary selection of *Petunia* X *hybrida* identified as code number TT20-K0749, not patented.

*Male, or pollen, parent.*—Proprietary selection of *Petunia* X *hybrida* identified as code number TT20-K0509, not patented.

Propagation:

*Type.*—By terminal vegetative cuttings.

*Time to initiate roots, summer.*—About five days at temperatures about 20C.

*Time to initiate roots, winter.*—About seven days at temperatures about 20C.

*Time to produce a rooted young plant, summer.*—About three weeks at temperatures about 20C.

*Time to produce a rooted young plant, winter.*—About four weeks at temperatures about 20C.

*Root description.*—Fine, fibrous; close to 155B in color, actual color of the roots is dependent on substrate composition, water quality, fertilizers, substrate temperature and age of roots.

*Rooting habit.*—Freely branching; dense.

Plant description:

*Plant and growth habit.*—Compact and uniformly mounding plant habit; freely branching habit with about five to six primary lateral branches each with about 10 to 16 secondary branches developing after pinching; moderately vigorous growth habit and moderate growth rate.

*Plant height, soil level to top of foliar plane.*—About 15 cm.

*Plant height, soil level to top of floral plane.*—About 15 cm.

*Plant diameter.*—About 35 cm.

Lateral branch description:

*Length.*—About 18 cm.

*Diameter.*—About 3 mm.

*Internode length.*—About 1 cm.

*Strength.*—Moderately strong.

*Aspect.*—Initially upright to somewhat outwardly spreading.

*Texture and luster.*—Pubescent; semi-glossy.

*Color, developing and developed.*—Close to 144A to 144B.

Leaf description:

*Arrangement.*—Before flowering, alternate; after flowering, opposite; simple.

*Length.*—About 4.3 cm.

*Width.*—About 2.2 cm.

*Shape.*—Spatulate.

*Apex.*—Obtuse.

*Base.*—Attenuate.

*Margin.*—Entire.

*Texture and luster, upper and lower surfaces.*—Pubescent; coriaceous; semi-glossy.

*Venation pattern.*—Pinnate; arcuate.

*Color.*—Developing leaves, upper surface: Close to 144A. Developing leaves, lower surface: Close to 144A to 144B. Fully expanded leaves, upper surface: Close to 137B; venation, close to 144A. Fully expanded leaves, lower surface: Close to 138A to 138; venation, close to 144B.

*Petioles.*—Length: About 4 mm. Diameter: About 3 mm. Strength: Moderately strong; firm. Texture and luster, upper and lower surfaces: Smooth, glabrous; matte. Color, upper surface: Close to 144B. Color, lower surface: Close to 144C.

Flower description:

*Flower type and flowering habit.*—Single salverform flowers arising from leaf axils; freely flowering habit with usually about 345 flowers and flower buds developing per plant during the flowering season; flowers face mostly upright to outwardly.

*Fragrance.*—None detected.

*Natural flowering season.*—Plants flower continuously during the spring and summer in Germany; early flowering habit, plants typically beginning flowering about nine weeks after planting.

*Flower longevity.*—Individual flowers last about two to three days on the plant; flowers persistent.

*Flower buds.*—Length: About 3.8 cm. Diameter: About 7 mm. Shape: Ovoid. Texture and luster: Rippled; semi-glossy. Color: Close to 145B and N79B.

*Flower diameter.*—About 5 cm by 5.2 cm.

*Flower depth* (*height*).—About 7.9 cm.

*Flower throat diameter.*—About 1 cm.

*Flower tube length.*—About 2.4 cm.

*Flower tube diameter, proximally.*—About 6 mm.

*Corolla.*—Arrangement: Five petals fused at the base and opening into a flared trumpet. Petal lobe length (from throat): About 2.4 cm. Petal lobe width: About 2.6 cm. Petal shape: Roughly spatulate. Petal apex: Obtuse, rounded. Petal margin: Entire; slightly undulate. Petal texture and luster, upper and lower surfaces: Rippled, glabrous; semi-glossy. Throat texture and luster: Rippled; semi-glossy. Tube texture and luster: Rippled; semi-glossy. Color: Petal lobe, when opening, upper surface: Close to 59A and N74A; star-shaped pattern, close to 155A. Petal lobe, when opening, lower surface: Close to N77B; star-shaped pattern, close to 157D. Petal lobe, fully opened, upper surface: Close to 72A and N74B; star-shaped pattern, close to 155B; venation, close to 150C to 150D; main color becoming closer to 72A to 72B and star-shaped pattern becoming closer to 155C with subsequent development. Petal lobe, fully opened, lower surface: Close to 77A; star-shaped pattern, close to 155B; venation, close to 154A; main color becoming closer to 77A to 77B and star-shaped pattern becoming closer to 155C with subsequent development. Flower throat: Close to 1D; venation, close to 145B. Flower tube: Close to 1C; venation, close to 145B.

*Sepals.*—Arrangement: Five sepals fused at the base forming a tubular star-shaped calyx. Length: About 2.4 cm. Diameter: About 2.9 mm. Shape: Oblong. Apex: Rounded. Base: Decurrent. Margin: Entire. Texture and luster, upper and lower surfaces: Smooth, glabrous; semi-glossy. Color: When opening and fully opened, upper surface: Close to 144A. When opening and fully opened, lower surface: Close to 144B.

*Peduncles.*—Length: About 2.3 cm. Diameter: About 1 mm. Strength: Moderately strong. Texture and luster: Smooth, glabrous; semi-glossy. Color: Close to 144A.

*Reproductive organs.*—Stamens: Quantity per flower: Five. Filament length: About 1.4 cm. Filament color: Close to 155C. Anther length: About 1 mm. Anther shape: Ovate. Anther color: Close to 93A. Pollen amount: Abundant. Pollen color: Close to 158A. Pistils: Quantity per flower: One. Pistil length: About 2.4 cm. Style length: About 1.9 cm. Style color: Close to 144D. Stigma diameter: About 1.5 mm. Stigma shape: Rounded. Stigma color: Close to 144A. Ovary color: Close to 143C. Fruits: Quantity produced per plant: About 200 during the flowering season. Length: About 5 mm. Diameter: About 5 mm. Texture: Smooth, glabrous. Color: Close to 161C. Seeds: Quantity per flower: About 80. Length: About 0.2 mm. Diameter: About 0.2 mm. Texture: Smooth, glabrous. Color: Close to 200A.

Garden performance: Plants of the new *Petunia* have been observed to have good garden performance and tolerate wind, rain, temperatures ranging from about 5C to about 40C and to be hardy to USDA Hardiness Zone 11.

Pathogen & pest resistance: Plants of the new *Petunia* have been observed to be resistant to Tobacco Mosaic Virus. To date, plants of the new *Petunia* have not been observed to be resistant to pests and other pathogens common to *Petunia* plants.

It is claimed:

1. A new and distinct *Petunia* plant named 'Dopetswepursta' as illustrated and described.

* * * * *